United States Patent
Michelson (10) Patent No.: US 8,105,383 B2
(45) Date of Patent: Jan. 31, 2012

(54) MANUFACTURED BONE COMPOSITE IMPLANT SHAPED TO CONFORM TO A PREPARED IMPLANTATION SPACE

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1459 days.

(21) Appl. No.: 11/089,087

(22) Filed: Mar. 24, 2005

(65) Prior Publication Data

US 2005/0171607 A1    Aug. 4, 2005

Related U.S. Application Data

(62) Division of application No. 09/593,591, filed on Jun. 13, 2000, now abandoned.

(51) Int. Cl.
*A61F 2/44* (2006.01)
(52) U.S. Cl. .................... 623/17.16; 623/17.11
(58) Field of Classification Search .... 623/17.11–17.16, 623/23.5, 23.51, 23.63
See application file for complete search history.

(56) References Cited

U.S. PATENT DOCUMENTS

| | | | |
|---|---|---|---|
| 3,867,728 A | 2/1975 | Stubstad et al. |
| D245,259 S | 8/1977 | Shen |
| 4,070,514 A | 1/1978 | Eatherly et al. |
| 4,309,777 A | 1/1982 | Patil |
| 4,349,921 A | 9/1982 | Kuntz |
| 4,599,086 A | 7/1986 | Doty |
| 4,714,469 A | 12/1987 | Kenna |
| 4,743,256 A | 5/1988 | Brantigan |
| 4,834,757 A | 5/1989 | Brantigan |
| 4,863,477 A | 9/1989 | Monson |
| 4,877,020 A | 10/1989 | Vich |
| 4,878,915 A | 11/1989 | Brantigan |
| 4,904,261 A | 2/1990 | Dove et al. |
| 4,911,718 A | 3/1990 | Lee et al. |
| 4,950,296 A | 8/1990 | McIntyre |
| 5,015,255 A | 5/1991 | Kuslich |

(Continued)

FOREIGN PATENT DOCUMENTS

CA    2 287 020 A1    10/1999

(Continued)

OTHER PUBLICATIONS

U.S. Appl. No. 09/593,591, filed Jun. 2000, Michelson.

(Continued)

*Primary Examiner* — Paul Prebilic
(74) *Attorney, Agent, or Firm* — Martin & Ferraro, LLP (57) ABSTRACT

The present invention is directed to a major long bone ring implant for insertion into an implantation space formed across a spinal disc between two adjacent vertebral bodies of the spine. The implantation space has a wall portion, lip, or ridge with a flat portion for abutting the leading end of the bone ring implant. The bone ring implant has a leading end and a trailing end connected by opposed sides. The leading end has a straight cut portion. The opposed sides have portions that are preferably straight and at a 90° angle to the straight cut portion of the leading end to produce straight portions that are outwardly facing. The bone ring implant may be machined from a single bone or manufactured from a composite of cortical fibers, filaments, or particles. The bone ring implant may be used in combination with lockable screws, and preferably screw locks each preferably made of cortical bone or of a bioresorbable material.

53 Claims, 3 Drawing Sheets

U.S. PATENT DOCUMENTS

| | | | |
|---|---|---|---|
| 5,062,845 | A | 11/1991 | Kuslich et al. |
| 5,071,437 | A | 12/1991 | Steffee |
| 5,123,926 | A | 6/1992 | Pisharodi |
| 5,192,327 | A | 3/1993 | Brantigan |
| 5,306,308 | A | 4/1994 | Gross et al. |
| 5,306,309 | A | 4/1994 | Wagner et al. |
| 5,338,772 | A | 8/1994 | Bauer et al. |
| 5,397,364 | A | 3/1995 | Kozak et al. |
| 5,425,772 | A | 6/1995 | Brantigan |
| 5,443,514 | A | 8/1995 | Steffee |
| 5,458,638 | A | 10/1995 | Kuslich et al. |
| 5,484,437 | A | 1/1996 | Michelson |
| 5,607,424 | A | 3/1997 | Tropiano |
| 5,669,909 | A | 9/1997 | Zdeblick et al. |
| 5,702,449 | A | 12/1997 | McKay |
| 5,766,252 | A | 6/1998 | Henry et al. |
| 5,814,084 | A | 9/1998 | Grivas et al. |
| 5,846,484 | A | 12/1998 | Scarborough et al. |
| 5,860,973 | A | 1/1999 | Michelson |
| 5,861,041 | A | 1/1999 | Tienboon |
| 5,865,845 | A | 2/1999 | Thalgott |
| 5,868,749 | A * | 2/1999 | Reed ................................ 606/76 |
| 5,888,227 | A | 3/1999 | Cottle |
| 5,899,939 | A * | 5/1999 | Boyce et al. ................ 623/16.11 |
| 5,972,368 | A | 10/1999 | McKay |
| 5,989,289 | A | 11/1999 | Coates et al. |
| 6,033,438 | A | 3/2000 | Bianchi et al. |
| 6,080,155 | A | 6/2000 | Michelson |
| 6,159,214 | A | 12/2000 | Michelson |
| 6,224,607 | B1 | 5/2001 | Michelson |
| 6,231,610 | B1 | 5/2001 | Geisler |
| 6,241,770 | B1 | 6/2001 | Michelson |
| 6,241,771 | B1 | 6/2001 | Gresser et al. |
| 6,245,108 | B1 | 6/2001 | Biscup |
| 6,258,125 | B1 | 7/2001 | Paul et al. |
| 6,277,149 | B1 | 8/2001 | Boyle et al. |
| 6,294,187 | B1 | 9/2001 | Boyce et al. |
| 6,350,283 | B1 | 2/2002 | Michelson |
| 6,371,988 | B1 | 4/2002 | Pafford et al. |
| 6,383,221 | B1 | 5/2002 | Scarborough et al. |
| 6,410,519 | B1 | 6/2002 | Gruskin et al. |
| 6,423,095 | B1 | 7/2002 | Van Hoeck et al. |
| 6,428,576 | B1 * | 8/2002 | Haldimann ................ 623/17.16 |
| 6,471,724 | B2 * | 10/2002 | Zdeblick et al. ............ 623/17.16 |
| 6,511,509 | B1 | 1/2003 | Ford et al. |
| 6,562,072 | B1 | 5/2003 | Fuss et al. |
| 6,610,065 | B1 | 8/2003 | Branch et al. |
| 6,645,206 | B1 | 11/2003 | Zdeblick et al. |
| 6,666,888 | B1 | 12/2003 | Jackson |
| 6,666,890 | B2 | 12/2003 | Michelson |
| 6,689,167 | B2 | 2/2004 | Bagby |
| 6,706,067 | B2 | 3/2004 | Shimp et al. |
| 6,709,458 | B2 | 3/2004 | Michelson |
| 6,749,636 | B2 | 6/2004 | Michelson |
| 6,827,740 | B1 | 12/2004 | Michelson |
| 6,902,581 | B2 | 6/2005 | Walkenhorst et al. |
| 6,989,031 | B2 | 1/2006 | Michelson |
| 7,022,137 | B2 | 4/2006 | Michelson |
| 7,077,866 | B2 | 7/2006 | Gresser et al. |
| 7,094,239 | B1 | 8/2006 | Michelson |
| 7,156,875 | B2 | 1/2007 | Michelson |
| 7,387,643 | B2 | 6/2008 | Michelson |
| 7,435,262 | B2 | 10/2008 | Michelson |
| 7,462,195 | B1 | 12/2008 | Michelson |
| 7,611,536 | B2 | 11/2009 | Michelson |
| 2002/0029081 | A1 | 3/2002 | Scarborough et al. |
| 2002/0111680 | A1 | 8/2002 | Michelson |
| 2002/0161442 | A1 | 10/2002 | Michelson |
| 2003/0130737 | A1 | 7/2003 | McGahan et al. |
| 2003/0195517 | A1 | 10/2003 | Michelson |
| 2004/0215203 | A1 | 10/2004 | Michelson |
| 2004/0230308 | A1 | 11/2004 | Michelson |
| 2004/0249388 | A1 | 12/2004 | Michelson |
| 2005/0004672 | A1 | 1/2005 | Pafford et al. |
| 2005/0171606 | A1 | 8/2005 | Michelson |
| 2005/0256574 | A1 | 11/2005 | Paul et al. |
| 2005/0267578 | A1 | 12/2005 | Michelson |
| 2006/0235519 | A1 | 10/2006 | Michelson |
| 2009/0105821 | A1 | 4/2009 | Michelson |

FOREIGN PATENT DOCUMENTS

| | | |
|---|---|---|
| DE | 35 05 567 A1 | 5/1986 |
| EP | 0 077 159 | 4/1983 |
| EP | 0 179 695 | 4/1986 |
| EP | 0 307 241 A2 | 3/1989 |
| EP | 0 517 030 A2 | 5/1992 |
| EP | 0 599 419 A2 | 6/1994 |
| EP | 0 627 204 A2 | 12/1994 |
| EP | 0 734 703 A2 | 10/1996 |
| ES | 283078 | 5/1985 |
| FR | 2 703 580 | 10/1994 |
| JP | 62-155846 | 7/1987 |
| WO | WO 93/01771 | 2/1993 |
| WO | WO 95/08964 | 4/1995 |
| WO | WO 97/25945 | 7/1997 |
| WO | WO 98/17209 | 4/1998 |
| WO | WO 98/44877 | 10/1998 |
| WO | WO 99/08627 | 2/1999 |
| WO | WO 00/24327 | 5/2000 |
| WO | WO 01/62191 | 8/2001 |
| WO | WO 01/82166 | 8/2001 |

OTHER PUBLICATIONS

Albee; "Bone Surgery with Machine Tools;" Scientific American; Apr. 1936; pp. 178-181.

Muschler, et al.; The Biology of Spinal Fusion: Spinal Fusion Science and Technique; Cotler and Cotler; pp. 9-13.

Zindrick, et al.; Lumbar Spine Fusion: Different Types and Indications; The Lumbar Spine, vol. 1, Second Edition, pp. 588-593 (1996).

Crock, H. V.; Practice of Spinal Surgery; Springer-Verlag/Wien, New York (1983).

Schmitz et al.; Performance of Alloplastic Materials and Design of an Artificial Disc; The Artificial Disc, Brock, Mayer, Weigel; pp. 23-34 (1991).

Fusion of the Lumbar Spine; Anterior Monosegmental Fusion L5-S1, Atlas of Spinal Operations, Thieme, pp. 270-274 (1993).

Lumbar Spine Surgery, Techniques & Complications; History of Lumbar Spine Surgery (1994) pp. 11-15; 27; 30; 35-45; 265-268.

European Opposition Document, Nov. 27, 1995—Opposing EP Patent No. 425 542 B1 to Karlin Technology, Inc.

Laparoscopic Bone Dowel Surgical Technique; Brochure of Sofamor Danek (1995).

Brochure of University of Flo9rida Tissue Bank; MD-I and MD-II Custom Machine Cortical Dowels; (Circa 1996).

Brochure of University of Florida Tissue Bank; MD-III Threaded Cortical Dowel; (Circa 1996).

Ray, C.D.; Spinal Interbody Fusions: A Review, Featuring New Generation Techniques; Neurosurgery Quarterly, 7(2):135-156 (1997).

A picture of a Medtronic, Sofamor Danek Display; titled "Evolving With Your Needs" (Apr. 6, 2000).

PCT International Search Report of International Application No. PCT/US01/14844, mailed Oct. 25, 2001.

Itoman, M., et al.; Banked Bone Grafting for Bone Defect Repair—Clinical Evaluation of Bone Union and Graft Incorporation; J. Jpn. Orthop. Assoc. 62;461-469 (1988).

* cited by examiner

MANUFACTURED BONE COMPOSITE IMPLANT SHAPED TO CONFORM TO A PREPARED IMPLANTATION SPACE

The present application is a divisional of application Ser. No. 09/593,591, filed Jun. 13, 2000 (now abandoned), which is incorporated herein by reference.

BACKGROUND OF THE INVENTION

The diaphysis is the shaft of a long bone, as distinguished from the epiphysis, the end of the bone forming the joints. When the diaphysis is cut twice, more or less transversely, a complete bone ring is formed with the medulary canal forming an opening through the ring. Such rings are generally harvested from femurs for use in the lumbar spine. Other bones from the arm or leg or other part of the skeleton may be useful in various regions of the spine.

The use of diaphyseal bone rings, such as those harvested from human femurs, is well known in the art of spinal fusion. For interbody spinal fusion, femoral rings are formed by making two spaced apart cuts approximately perpendicular to the long axis of the diaphyseal portion of a human cadaveric femur. The cuts are generally spaced apart so as to form a ring having a height corresponding to the restored disc space or slightly greater. Femoral ring bone grafts are placed into the spine within and across the height of the space previously occupied by a spinal disc between adjacent vertebral bodies to achieve interbody fusion of those vertebral bodies through the disc space. The femoral ring bone graft is incorporated into the bony fusion over time.

Interbody spinal fusion with bone rings, however, has had limited success in the past. While all the causes for failure may not yet be appreciated, it is nevertheless believed that a failure to gain congruity at the interfaces of the bone ring implant to the adjacent vertebral bodies, and a failure to achieve stability of the bone ring implant, may be two of the more significant factors subject to the surgeon's control contributing to such failures.

Bone rings that are entirely or almost entirely made of cortical bone offer the advantages of that material including an appropriate modulus of elasticity and strength for the prescribed use, the capacity to be bioactive, including being osteoconductive, osteoinductive, osteogenic, and to more generally provide a good substrate for the formation of new bone as fusion occurs. Further, by being bioabsorable the bone material is replaced by the patient's own bone over time, thereby preventing stress shielding and leading to the eventual elimination of any foreign body from the implantation site.

As it is desirable to take advantage of all these benefits, there exists a need for an improved bone ring implant, which when used in accordance with the prescribed method of disc space preparation, provides for an improved congruity of the implant to the vertebral bodies and improved implant stability.

SUMMARY OF THE INVENTION

The present invention is directed to a major long bone ring implant preferably, but not necessarily, an implant formed from a diaphyseal ring for insertion into an implantation space formed across a spinal disc between two adjacent vertebral bodies of the spine. The bone ring implant is preferably used in an implantation space having a wall portion, lip, or ridge with a flat portion for abutting the leading end of the bone ring implant. Such an implantation space can be formed with the instrumentation and method set forth in applicant's U.S. application Ser. No. 08/688,758. titled "Milling Instrumentation and Method for Preparing a Space Between Adjacent Vertebral Bodies", incorporated by reference herein. It is appreciated however, that the bone ring implant of the present invention can be useful in implantation spaces formed by other techniques, such as for example, applicant's U.S. application Ser. No. 09/490,901, titled "Instrument And Method For Creating An Intervertebral Space For Receiving An Implant", incorporated by reference herein.

The bone ring implant is manufactured and machined to have a leading end and a trailing end opposite the leading end connected by opposed sides or walls. In combination the leading end, trailing end, and the opposed sides or walls preferably form one continuous perimeter having opposed upper and lower vertebral body engaging surfaces. By way of example and not limitation, while diaphyseal rings as harvested are generally round or oval, the bone ring implants of the present invention have a substantial flat portion at the leading end formed by cutting or machining the perimeter of the bone to create a straight cut portion at the leading end. The straight cut portion is generally oriented at 90° to the mid-longitudinal axis of the bone ring implant as defined by a line passing through the center of the bone ring implant from its leading end to its trailing end.

In a preferred embodiment, the bone ring implant is further machined so that one and preferably both of the opposed sides have portions that are straight and at a 90° angle to the straight cut portion of the leading end to produce straight portions that are outwardly facing. These straight portions are generally oriented parallel to the implant's longitudinal axis. The opposed sides may be machined to be generally parallel to each other over at least a portion of the sides and may be aligned or offset from each other along the implant sides. The present invention consists of the unique machined structures of the bone ring implant, as well as may be used in combination with lockable screws, and preferably screw locks each preferably made of cortical bone or of a bioresorbable material.

The bone ring implant of the present invention may be machined so as to be adapted to receive through its trailing end at least a pair of opposed appropriately sized bone screws preferably, but not necessarily, made of cortical bone. The bone engaging screws may be aligned or offset from each other. At least one screw engages each of the vertebral bodies adjacent a disc space to be fused and into which the bone ring implant is implanted.

The bone ring implant of the present invention is preferably further machined and adapted to receive locks, preferably made of cortical bone, at the trailing end for securing the bone engaging screws therein and preventing the screws from backing out. The bone ring implant, bone screws, and/or locks can be made of a bioresorbable material, including but not limited to cortical bone, plastics and composite plastics. Suitable plastics may include those comprising lactides, galactides, glycolide, capronlactone, trimethylene carbonate, or dioxanone in various polymers, and/or combinations thereof.

The bone ring implant of the present invention can be further machined to have a specialized bone engaging surface configuration designed to enhance stability and resist motion imparted to each of the opposed upper and lower vertebrae engaging surfaces of the bone ring implant, such as for example the surface described in applicant's U.S. application Ser. No. 09/457,228 titled "Spinal Implant Surface Configuration" incorporated by reference herein.

The bone ring implant of the present invention is preferably for anterior implantation into the disc space and is preferably taller at the trailing end than at the leading end (the leading end being adapted to introduce the implant into the spine) so as to provide for a desired amount of lordosis.

The bone ring implant has been described as diaphyseal rings by way of example of one embodiment of the present invention. It should be clearly understood that such rings may be formed of bone that may be at least in part metaphyseal if sufficiently strong for the intended purpose. Alternatively, the bone ring implants may be made of a manufactured bone composite comprising of particles or filaments of bone and a bioresorbable plastic or ceramic or other suitable material without departing from the inventive concepts of the present invention, prime of which is a manufactured implant comprising cortical bone with a flat leading portion and preferably at least partial side portions that are flat and preferably 90° to the front of the implant.

OBJECTS OF THE PRESENT INVENTION

It is an object of an embodiment of the present invention to provide a manufactured bone ring implant having an improved contour and conformation with critical known dimensions.

It is a further object of an embodiment of the present invention to have the bone ring implant configuration conform, where critical, to an easily and reliably producible shape of an interbody recipient site.

It is a further object of an embodiment of the present invention to have opposed upper and lower vertebral body engaging surfaces configured to enhance the stability of the bone ring implant relative to the adjacent vertebral bodies when in use.

In a preferred embodiment of the present invention, it is a further object of the present invention to provide for an improved cortical bone ring implant adapted to receive at least a pair of opposed vertebral body engaging bone screws for further stabilizing the bone ring implant, and for stabilizing the adjacent vertebrae relative to the bone ring implant and to each other.

It is a further object of an embodiment of the present invention to provide for an interbody spinal fusion implant in the form of an improved ring of diaphyseal bone from a human long bone correspondingly dimensioned for a recipient site across the height of a disc space and in contact with each of the vertebral bodies adjacent that disc space.

It is a further object of an embodiment of the present invention to provide for an improved bone ring implant adapted to receive screw locks for locking opposed vertebral body engaging bone screws to the bone ring implant to prevent them from backing out.

DETAILED DESCRIPTION OF THE DRAWINGS

Figure 1:
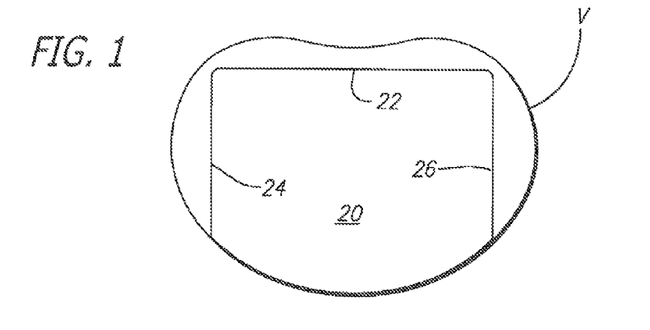
FIG. 1 is a top plan view of a vertebral body with preferably a machined implantation socket created therein for receiving a bone ring implant in accordance with the present invention.

FIG. 1 shows a top plan view of a vertebral body V with an implantation space 20 created therein for receiving an implant. Implantation socket or space 20 has a posterior wall 22 and side walls 24, 26 formed at least in part in the endplate of vertebral body V. By way of example and not limitation, implantation space 20 may be created with the apparatus and methods disclosed in applicant's U.S. application Ser. No. 08/688,758.

Figure 2A:
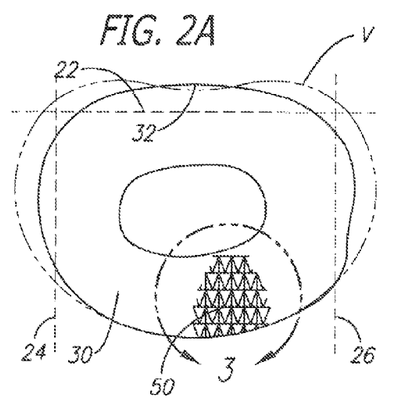
FIG. 2A is a top plan view of a vertebral body showing the desired implantation socket with a first bone ring implant with a bone-engaging surface formed thereon and showing the machining of the bone ring required to obtain that ring's best fit to the recipient site (socket) within that vertebral body.
Figure 2B:
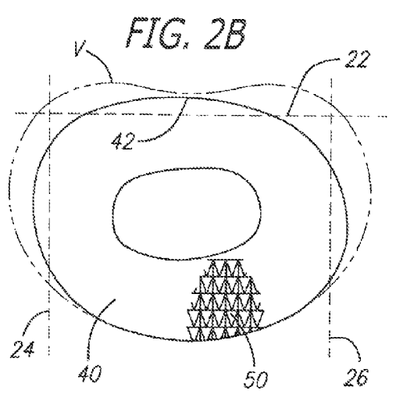
FIG. 2B is a top plan view of a vertebral body showing the desired implantation socket with a second bone ring implant with the bone-engaging surface formed thereon and showing the machining of the bone ring required to obtain that ring's best fit to the recipient site (socket) within that vertebral body.

FIGS. 2A and 2B show top plan views of vertebral body V and first and second bone ring implants 30 and 40, respectively, placed thereon with the area of implantation space 20 identified by dotted lines. Bone rings can be made from a long bone of the human body, and preferably made from a human femur. First and second bone ring implants 30, 40 have outer perimeters that are intact and not modified from their naturally occurring state such as in a human femur. Bone ring implants 30, 40 in their natural state do not fit properly within the prepared implantation space 20 bordered by posterior wall 22 and side walls 24, 26 illustrated by the dotted lines. Bone ring implant 30 has sides that extend beyond side walls 24, 26 and a leading end 32 that extends beyond posterior wall 22 of implantation space 20 and protrudes from the posterior aspect of vertebral body V. Similarly, while bone ring implant 40 does not protrude from the posterior aspect of vertebral body V, leading end 42 extends beyond posterior wall 22 and has sides that extend beyond side walls 24, 26 of implantation space 20.

Figure 3A:
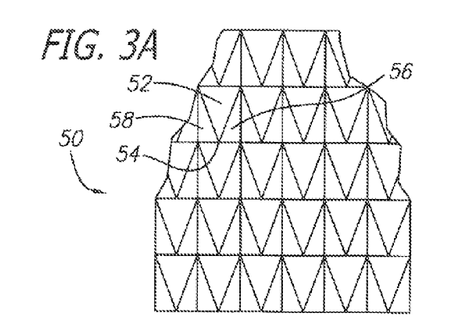
FIG. 3A is an enlarged fragmentary view along line 3-3 of FIG. 2A of the bone-engaging surface.
Figure 3B:
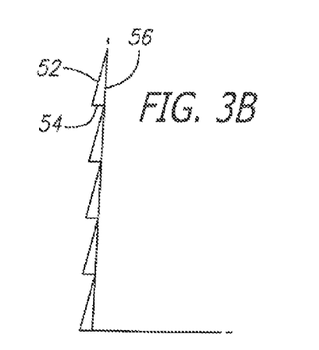
FIG. 3B is a side view of FIG. 3A illustrating the configuration of the bone-engaging surface.

FIG. 3A shows an enlarged fragmentary view of a bone-engaging surface 50 that can be formed on bone ring implants described herein to increase the stability of the bone ring implants installed between two adjacent vertebral bodies. FIG. 3B is a side view of FIG. 3A illustrating the configuration of a preferred embodiment of bone-engaging surface 50. Bone engaging surface 50 has a forward facet 52 facing the leading end of the bone ring implant, an opposite rearward portion 54 facing the trailing end of the bone ring implant, and opposed side facets 56, 58 directed generally toward the sides of the bone ring implant. Bone engaging surface 50 preferably facilitates motion in the direction of insertion and preferably resists motion in all other directions, including the direction opposite to the direction of insertion. While the specialized bone-engaging surface 50 is preferred, in the alternative the surfaces of the bone ring can be roughened, ratcheted, knurled, or otherwise modified when it is desired to increase the resistance of the bone ring implant to motion.

FIGS. 4-10 show a bone ring implant 100 in accordance with various preferred embodiments of the present invention. Bone ring implant 100 has a leading end 102 for Insertion into the Implantation space, an opposite trailing end 104, a mid-longitudinal axis MLA passing through the leading and trailing ends, opposed upper and lower surfaces 106, 108, and opposed sides, 110, 112 therebetween. In the embodiment shown in FIG. 10. trailing end 104 has a non-linear portion and opposed sides 110, 112 have straight portions, which may be parallel to each other. Upper and lower surfaces 106,108 include a medulary canal 114 passing therethrough which may be useful to permit for the growth of bone from adjacent vertebral body to adjacent vertebral body through the medulary canal 114 in bone ring Implant 100, which can to that end be filled with fusion promoting substances. Upper and lower surfaces 106, 108 may also be porous or include a bone ingrowth surface.

In a preferred embodiment of the present invention, leading end 102 and opposed sides 110, 112 are machined to configure bone ring implant 100 to conform to the shape of prepared implantation space 20. Leading end 102 and sides 110, 112 can be machined to have a more planar configuration to abut posterior wall 22 and side walls 24, 26, respectively, of implantation space 20. In this embodiment, the machined surfaces of leading end 102 and opposed sides 110, 112 are separated by the natural contour of the bone ring. For example, in a preferred embodiment, the bone ring implant 100 can be machined so either or both of sides 110, 112 are at a 90° angle to the straight cut portion of leading end 102 to produce straight portions outwardly facing and generally parallel to each other, that can be aligned or offset from each other along sides 110, 112.

Alternatively, in another embodiment of the present invention, instead of being machined from a single bone, the bone ring implant can be manufactured from a composite of cortical fibers, filaments, particles, and a material which may or may not be bioactive and/or bioresorbable such as a plastic, ceramic, for example. Once formed, the composite implant material may be machined or molded, into the desired shape.

Figure 4:
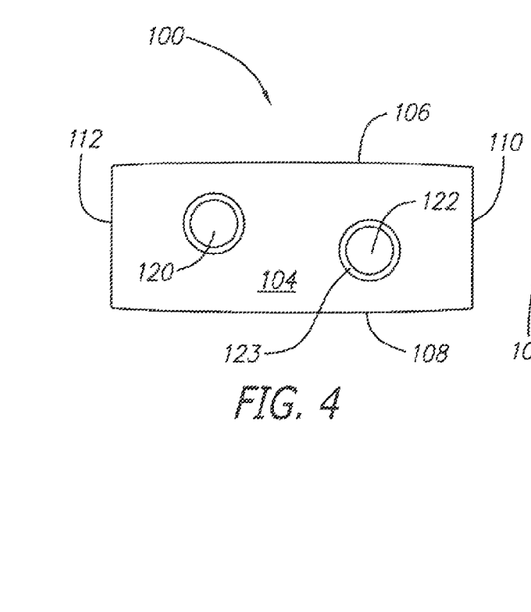
FIG. 4 is a trailing end view of a bone ring implant in accordance with an embodiment of the present invention having openings oriented toward the adjacent vertebral bodies for receiving bone-engaging screws.
Figure 5:
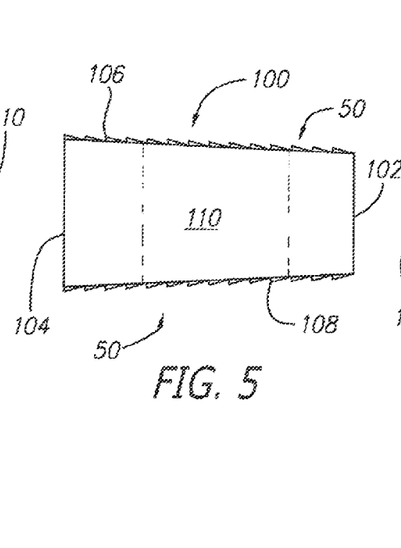
FIG. 5 is a side elevation view of the bone ring implant of FIG. 4.
Figure 6:
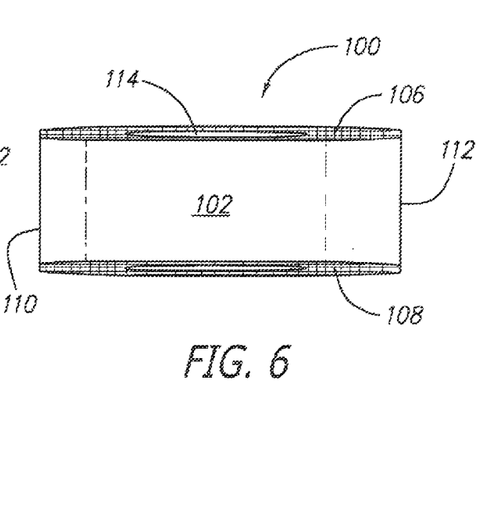
FIG. 6 is a leading end view of the bone ring implant of FIG. 4.
Figure 7:
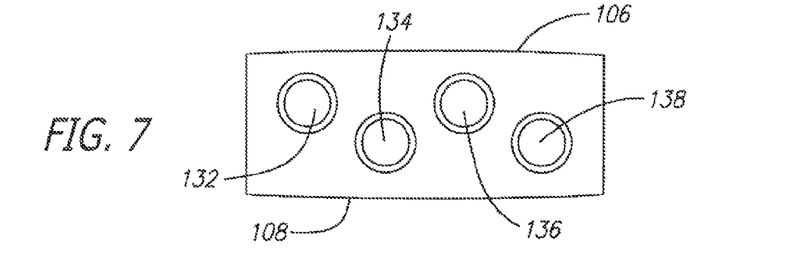
FIG. 7 is a trailing end view of a bone ring implant in accordance with a second embodiment of the present invention.
Figure 8:
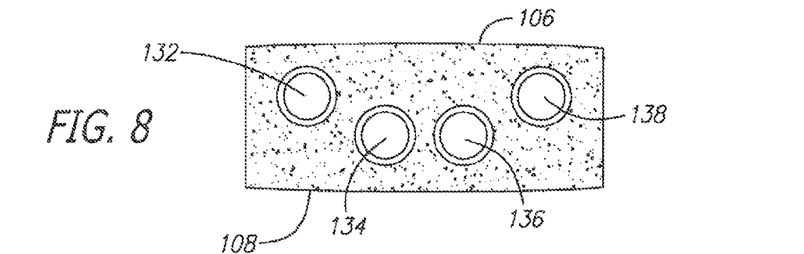
FIG. 8 is a trailing end view of a bone ring implant in accordance with a third embodiment of the present invention.
Figure 9:
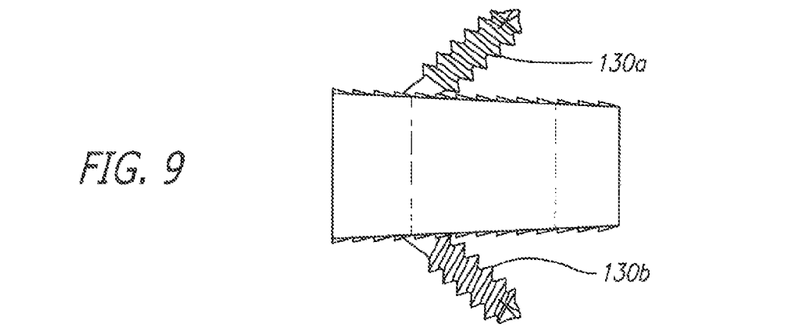
FIG. 9 is a side elevation view of the bone ring implant of FIG. 6 with two bone engaging screws installed.
Figure 10:
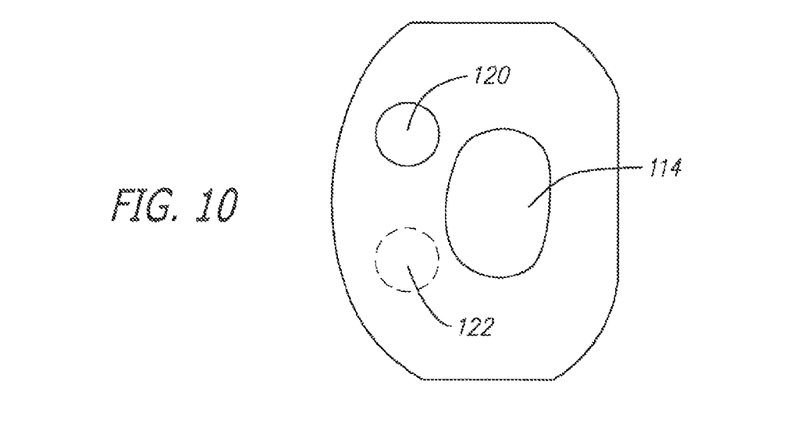
FIG. 10 is a top plan view of the bone ring implant of FIG. 6 machined to have a top exit screw hole and a bottom exit screw hole shown in hidden line.

As shown in FIGS. 4, 9, and 10, in a preferred embodiment of the present invention, trailing end 104 can be machined to include openings 120, 122 for receiving bone-engaging screws 130a, 130b. Openings 120, 122 extend from trailing end 104 through upper and lower surfaces 106, 108, respectively, and are preferably oriented or directed toward the adjacent vertebral bodies. As shown in FIGS. 7 and 8, instead of openings 120, 122, trailing end 104 can include openings 132, 134, 136, 138, for receiving bone-engaging screws. Openings 132, 134, 136, 138 can be oriented toward upper and lower surfaces 106, 108 in an alternating manner as shown in FIG. 7. Alternatively, openings 132, 138 can be oriented toward upper surface 106 and openings 134, 136 can be oriented toward lower surface 108 as shown in FIG. 8, or any combination thereof. The number of openings in trailing end 104 can vary depending on the size of the implant and the number of screws desired to be utilized by the surgeon.

In a further embodiment of the present invention, the medulary canal 114 of bone ring implant 100 may be loaded with fusion promoting substances and/or the implant may be treated with fusion promoting substances. Such substances may include, but are not limited to, bone morphogenetic protein (BMP), genetic material coding for the production of bone, mineralizing proteins, bone or bone products, a chemical substance to inhibit scar formation, and other materials.

In a further embodiment of the present invention, the medulary canal 114, which may or may not be machined, is compressively loaded with what is at least in part fusion promoting substances to increase the density of the filled area. Potentially, this allows for an increase in the quantities of fusion promoting material and provides the ability of the filled area to bear load.

The bone ring implants, bone screws, or locks could include a bioresorbable material including, but not limited to cortical bone, plastics and composite plastics. Suitable plastics may include those comprising lactides, galactides, glycolide, capronlactone, trimethylene carbonate, dioxanone in various polymers and/or combinations.

The present invention has been described as being an improved ring of bone harvested from the diaphyseal region of a long bone. This has been done to emphasize that the implant should have a substantial ring or perimeter of cortical bone. It is not necessary that the perimeter of cortical bone be uninterrupted or complete. The perimeter of the bone ring implant may include an open portion adapted to provide access to the medulary canal 114. Further, the implant could rely on some portion of denser cancellous bone and still conform to the teachings of the present invention. The present invention can include bone harvested from the area of the diaphyseal/metaphyseal transition. If the cancellous density of a specific bone were sufficient for the graft to work in the intended manner, then a graft could be harvested from the metaphyseal region of that bone and machined in accordance with the teachings of the present invention and would be within the scope of the present invention.

While a preferred embodiment of the present invention has been described in regard to a femoral ring modified in accordance with the teachings of the present invention, the invention itself is not so limited. While a femoral ring, because of its diameter, lends itself well to use in the human adult lumbar spine, other tubular bones may be useful in various locations of a human spine. By way of example only and not limitation, rings formed through the diaphyseal region of a fibula or humerus may be used for interbody fusion in the cervical spine, while a tibial ring may be used in the thoracic or lumbar spine. Finally, the implants of the present invention may be formed from a composite material comprising cortical bone.

What is claimed is:

1. An interbody spinal implant made of a bone composite material for insertion at least in part into an implantation space formed across the height of a disc space between adjacent vertebral bodies of a human spine and into at least a portion of the endplates of the vertebral bodies, the implantation space having a front wall, said implant comprising:

a body manufactured from a bone composite material, said body having a perimeter with a leading end, a trailing end opposite said leading end, and opposite exterior sides, said body having a mid-longitudinal axis passing through said leading and trailing ends, said leading end having a straight portion in a direction from one of said opposite exterior sides to another of said opposite exterior sides along a portion of the perimeter of said body adapted to abut the front wall of the implantation space when said implant is installed into the implantation space;

opposite upper and lower surfaces adapted to be placed in contact with and to support the adjacent vertebral bodies, said upper and lower surfaces being non-arcuate;

said opposite exterior sides connecting said upper and lower surfaces and said leading and trailing ends, said opposite exterior sides of said implant having straight portions that are parallel to each other; and an opening passing through said upper and lower surfaces for permitting for the growth of bone from adjacent vertebral body to adjacent vertebral body through said implant, said opening being between said straight portions of said opposite exterior sides and having a maximum width transverse to the mid-longitudinal axis of said body, said trailing end having a non-linear portion between two lines parallel to the mid-longitudinal axis, the parallel lines being spaced apart from one another on opposite sides of the mid-longitudinal axis and intersecting the maximum width of said opening; and wherein said implant is in combination with at least one bone screw adapted to engage at least one vertebral body when inserted through said implant, said implant comprising a lock for locking said at least one bone screw to said implant, said lock being made of one of cortical bone and a bioresorbable material.

2. The implant of claim 1, wherein said straight portion of said leading end is generally oriented at 90 degrees to the mid-longitudinal axis of the implant.

3. The implant of claim 1, wherein said straight portion of said at least one side is generally oriented 90 degrees to said straight portion of said leading end.

4. The implant of claim 1, wherein said straight portion of said at least one side is oriented generally parallel to the mid-longitudinal axis of said implant.

5. The implant of claim 1, further comprising at least one protrusion extending from at least one of said upper and lower surfaces for engaging at least one of the adjacent vertebral bodies to maintain said implant within the implantation space.

6. The implant of claim 5, wherein said protrusion comprises at least one of a ridge, ratcheting, spline, and knurling.

7. The implant of claim 1, wherein said upper and lower surfaces are porous.

8. The implant of claim 1, wherein said upper and lower surfaces include a bone ingrowth surface.

9. The implant of claim 1, wherein the perimeter of said body forms at least a portion of a ring.

10. The implant of claim 1, wherein said implant has a closed perimeter.

11. The implant of claim 1, wherein said implant has an open perimeter for providing access to said opening.

12. The implant of claim 1, wherein said implant is generally rectangular in shape.

13. The implant of claim 1, wherein said implant is generally oval in shape.

14. The implant of claim 1, wherein at least a portion of said upper and lower surfaces are in an angular relationship to each other from trailing end to leading end for allowing angulation of the adjacent vertebral bodies relative to each other.

15. The implant of claim 1, wherein at least a portion of said leading end is tapered for facilitating insertion of said implant between the two adjacent vertebral bodies.

16. The implant of claim 1, wherein said implant is adapted for insertion from the anterior aspect of the vertebral bodies and said trailing end is configured to conform to the anatomic contour of at least a portion of the anterior aspect of the vertebral bodies.

17. The implant of claim 1, wherein said implant has a maximum length less than and approximating the posterior to anterior depth of the vertebral bodies.

18. The implant of claim 1, wherein said implant has a width greater than one half the width of the adjacent vertebral bodies.

19. The implant of claim 1, wherein said opening is compressively loaded with fusion promoting material.

20. The implant of claim 1, further comprising at least a second opening passing through said upper and lower surfaces for permitting for the growth of bone from adjacent vertebral body to adjacent vertebral body through said implant.

21. The implant of claim 20, wherein said second opening communicates with said opening.

22. The implant of claim 1, further comprising a plurality of openings and passages adapted to retain a fusion promoting substance.

23. An interbody spinal implant made of a bone composite material for insertion at least in part into an implantation space formed across the height of a disc space between adjacent vertebral bodies of a human spine and into at least a portion of the endplates of the vertebral bodies, the implantation space having a front wall, said implant comprising:

a body manufactured from a bone composite material, said body having a perimeter with a leading end, a trailing end opposite said leading end, and opposite exterior sides, said body having a mid-longitudinal axis passing through said leading and trailing ends, said leading end having a straight portion in a direction from one of said opposite exterior sides to another of said opposite exterior sides along a portion of the perimeter of said body adapted to abut the front wall of the implantation space when said implant is installed into the implantation space;

opposite upper and lower surfaces adapted to be placed in contact with and to support the adjacent vertebral bodies, said upper and lower surfaces being non-arcuate;

said opposite exterior sides connecting said upper and lower surfaces and said leading and trailing ends, said opposite exterior sides of said implant having straight portions that are parallel to each other; and an opening passing through said upper and lower surfaces for permitting for the growth of bone from adjacent vertebral body to adjacent vertebral body through said implant, said opening being between said straight portions of said opposite exterior sides and having a maximum width transverse to the mid-longitudinal axis of said body, said opening having a perimeter, a majority of said perimeter of said opening being non-linear, said trailing end having a non-linear portion between two lines parallel to the mid-longitudinal axis, the parallel lines being spaced apart at a distance from one another on opposite sides of the mid-longitudinal axis and intersecting the maximum width of said opening, said non-linear portion of said trailing end extending across a majority of the distance between the parallel lines;

wherein said implant is in combination with at least one bone screw adapted to engage at least one vertebral body when inserted through said implant, said implant comprising a lock for locking said at least one bone screw to said implant, said lock being made of one of cortical bone and a bioresorbable material.

24. The implant of claim 1, wherein said at least one bone screw is made of one of cortical bone and a bioresorbable material.

25. The implant of claim 1, wherein said composite material includes filaments of bone.

26. The implant of claim 1, wherein said composite material includes a bioresorbable plastic.

27. The implant of claim 1, wherein said composite material includes ceramic.

28. The implant of claim 1, further in combination with fusion promoting substances.

29. The implant of claim 1, in combination with a fusion promoting material other than bone.

30. The implant of claim 1, wherein said implant comprises a bone ingrowth material other than bone.

31. The implant of claim 1, further comprising a material, other than the bone from which said implant is formed, that intrinsically participates in the growth of bone from one of the adjacent vertebral bodies to the other of the adjacent vertebral bodies.

32. The implant of claim 29, wherein said fusion promoting material is bone morphogenetic protein.

33. The implant of claim 1, further in combination with bone morphogenetic protein.

34. The implant of claim 1, further in combination with an osteogenic material.

35. The implant of claim 34, wherein said osteogenic material is a material other than bone.

36. The implant of claim 35, wherein said material is genetic material coding for the production of bone.

37. The implant of claim 1, further in combination with genetic material coding for production of bone.

38. The implant of claim 1, in combination with a chemical substance to inhibit scar formation.

39. The implant of claim 23, wherein said straight portion of said leading end is generally oriented at 90 degrees to the mid-longitudinal axis of the implant.

40. The implant of claim 23, wherein said straight portion of said at least one side is generally oriented 90 degrees to said straight, portion of said leading end.

41. The implant of claim 23, further comprising at least one protrusion extending from at least one of said upper and lower surfaces for engaging at least one of the adjacent vertebral bodies to maintain said implant within the implantation space.

42. The implant of claim 41, wherein said protrusion comprises at least one of a ridge, ratcheting, spline, and knurling.

43. The implant of claim 41, wherein said at least one protrusion is configured to facilitate motion of said implant in a direction of insertion into the implantation space and resist motion in a direction opposite to the direction of insertion.

44. The implant of claim 23, wherein said implant has a closed perimeter.

45. The implant of claim 23, wherein said implant has an open perimeter for providing access to said opening.

46. The implant of claim 23, wherein at least a portion of said upper and lower surfaces are in an angular relationship to each other from trailing end to leading end for allowing angulation of the adjacent vertebral bodies relative to each other.

47. The implant of claim 23, wherein at least a portion of said leading end is tapered for facilitating insertion of said implant between the two adjacent vertebral bodies.

48. The implant of claim 23, wherein said implant has a width greater than one half the width of the adjacent vertebral bodies adjacent the implantation space into which said implant is to be inserted.

49. The implant of claim 23, further comprising at least a second opening passing through said upper and lower surfaces for permitting for the growth of bone from adjacent vertebral body to adjacent vertebral body through said implant.

50. The implant of claim 23, further in combination with fusion promoting substances.

51. The implant of claim 50, wherein said fusion promoting includes at least one of bone, bone morphogenetic protein, and genetic material coding for the production of bone.

52. The implant of claim 23, further in combination with a chemical substance to inhibit scar formation.

53. The implant of claim 23, wherein said trailing end includes at least two bone screw openings, each of said bone screw openings being adapted to receive a bone screw.

\* \* \* \* \*

UNITED STATES PATENT AND TRADEMARK OFFICE
CERTIFICATE OF CORRECTION

| | | |
|---|---|---|
| PATENT NO. | : 8,105,383 B2 | Page 1 of 1 |
| APPLICATION NO. | : 11/089087 | |
| DATED | : January 31, 2012 | |
| INVENTOR(S) | : Gary K. Michelson | |

It is certified that error appears in the above-identified patent and that said Letters Patent is hereby corrected as shown below:

<u>Title Page 2, item (56), Other Publications</u>:
Column 2, line 35: change "pp. 9-13." to -- pp. 9-13, published December 21, 1989. --.

<u>Column 9, Line 31</u>:
Change "straight," to -- straight --.

Signed and Sealed this
Thirty-first Day of July, 2012

David J. Kappos
*Director of the United States Patent and Trademark Office*